United States Patent
Bokade et al.

(10) Patent No.: US 7,202,390 B2
(45) Date of Patent: Apr. 10, 2007

(54) PROCESS FOR PRODUCTION OF CUMENE

(75) Inventors: Vijay Vasant Bokade, Maharashtra (IN); Ulhas Kanhaiyalal Kharul, Maharashtra (IN)

(73) Assignee: Council of Scientific and Industrial Research, New Delhi (IN)

(*) Notice: Subject to any disclaimer, the term of this patent is extended or adjusted under 35 U.S.C. 154(b) by 359 days.

(21) Appl. No.: 10/620,813

(22) Filed: Jul. 17, 2003

(65) Prior Publication Data
US 2005/0014982 A1 Jan. 20, 2005

(51) Int. Cl.
*C07C 2/66* (2006.01)
(52) U.S. Cl. .................................. 585/467; 585/446
(58) Field of Classification Search ............... 585/467, 585/446
See application file for complete search history.

(56) References Cited

U.S. PATENT DOCUMENTS 5,100,596 A * 3/1992 Haag et al. .................. 264/42
5,474,681 A * 12/1995 Fehlner et al. ............ 210/500.25
5,932,104 A * 8/1999 Kawamura ................. 210/651

FOREIGN PATENT DOCUMENTS

| EP | 0537389 A | 4/1993 |
| EP | 0538518 A | 4/1993 |
| WO | WO 01/62692 A | 8/2001 |

* cited by examiner

Primary Examiner—Thuan Dinh Dang
(74) Attorney, Agent, or Firm—Nixon & Vanderhye, P.C.

(57) ABSTRACT

This invention related to an improved process for preparation of cumene. More particularly, the present invention relates to a process for the preparation of cumene using catalytic membrane reactors. The membrane used in the process facilitates reaction in a forward direction such that byproduct formation is reduced or eliminated.

29 Claims, 2 Drawing Sheets

PROCESS FOR PRODUCTION OF CUMENE

FIELD OF THE INVENTION

This invention related to an improved process for preparation of cumene. More particularly, the present invention relates to a process for the preparation of cumene using catalytic membrane reactors. The membrane used in the process facilitates reaction in a forward direction such that byproduct formation is reduced or eliminated.

BACKGROUND OF THE INVENTION

Cumene is widely used in many chemical industries for the manufacture phenol, acetone, α-methyl styrene, etc.

In the prior art, various processes are demonstrated for the preparation of cumene. Normally alkylation of benzene to cumene is done by Friedel-Crafts alkylation route. The Friedel-Crafts alkylation reaction is catalyzed by both protons (e g. $H_3PO_2$) and Lewis acids (e.g. $BF_3$) on different supports, such as amorphous and crystalline aluminosillicates. The reaction proceeds through activation of the olefin which then reacts with benzene. Riedel type of mechanism proposed interaction between free benzene molecule and activated olefin molecule attached to an active site ("Friedel Craft Alkylation Chemistry", Robert R. and Khalaf, A., Marcel Dekker Inc. New York, 1984).

U.S. Pat. No. 4,169,111, 1997 teaches isopropylation of benzene in a liquid phase catalytic reaction and is operated at very close to critical conditions of the reactants isoproplyl alcohol (IPA) and benzene. Harper et al, '*Industrial and Laboratory Alkylations*' (edited by L. F. Albrith and A. R. Goldsby, ACS Symposium Series, 55, 371, ACS, Washington D.C., 1977) studied the kinetics of the reaction. The equilibrium constant for the transalkylation reaction decreases with increasing temperatures. This means that the cumene content at equilibrium is favored by decreasing the temperature, although the effect is not particularly good.

The two processes most widely used on industrial scale are UOP's Cumox process (U.S. Pat. No. 4,128,593, 1978) and Monsanto-Lummus Cumene process (T. Vett, 'Monsanto Lummus styrene process is efficient' *Oil & Gas Journal*, 76 July 1981). The Cumox process for the production of phenol is accomplished via UOP's catalytic condensation process for cumene. The process utilizes a solid phosphoric acid (SPA) catalyst. In this process a mixture of propylene with excess benzene is pumped upwards in the alkylation reactor filled with SPA catalyst. The reactor effluent is routed through a two stage flash system prior to the final fractionator. Excess of the benzene gets separated in the flash system and is recycled back to the alkylation reactor. Cumene as a major product is separated in the fractionation column. The bottom from the fractionator comprises highly aromatic material containing mainly diisopropylbenzene (DIPB) isomers. The DIPB is reacted back with, benzene in a mole ratio of 1:8 to obtain cumene in a transalkylation reactor. A very small and regulated amount of water is added to the feed in order to keep the catalyst away from becoming friable and disintegratable. The process offers 99.3% by wt. conversion of propylene with 92.5% selectivity to cumene.

In Monsanto-Lummus Crest process, dry benzene and propylene are mixed in the alkylation reactor with a aluminium chloride hydrogen—chloride catalyst at controlled temperature, catalyst concentration and residence time. The reactor effluent is washed with water and caustic to separate the organics from strongly acidic catalyst. Major features of this process are low benzene recycle ratio.

A process using zeolite catalyst is also demonstrated (U.S. Pat. No. 5,687,540). According to this process, a heterogeneous catalyst (large pore 12 membered ring zeolite-β) based process was used for the production of cumene by isopropylation of benzene using isopropyl alcohol. The process uses a mole ratio of IPA: benzene of 1:6, catalyst volume of 4 cc per 100 cc of reactor volume and space velocity of 2.5 $h^{-1}$. The two processes described above (UOP and Monsanto) use isopropylene (which is usually obtained from isopropanol) as the reagent while the process, of this patent uses isopropanol directly, thereby reducing one step of isopropanol dehydration to isopropylene. In addition isopropanol is more stable than isopropylene at reaction condition. The use of isopropanol prolongs the life of the catalyst.

The processes documented in the literature and as discussed above however, have several drawbacks. The Cumos process uses excess of benzene, which needs to be separated by flash condensation and then needs to be recycled. The flash condensation involves additional operating cost. Also a higher reactant mole ratio is required. The formed cumene needs to be separated by using large distillation columns. Isomers of DIOB are formed as byproducts, which need to be transalkylated to cumene. This involves additional transalkylation reactor. The catalyst used in the process is corrosive and creates environmental pollution. In addition water needs to be added to keep the catalyst away from becoming friable and disintegrating. The Monsanto process uses strong acid catalyst, which is corrosive in nature. The reactor effluent in this process needs to be washed with water and caustic in order to separate organics. The process using zeolite catalyst also suffers from certain drawbacks like requirement of higher catalyst volume, higher reactant mole ratio and byproduct formation (e.g. DIPB isomers, toluene, $C_8$, $C_{10}$ and $C_{11}$ aromatics, n-propyl benzene, high boiling fractions). The processes documented in the literature thus have several drawbacks like high catalyst volume, high feed mole ratio, lower space velocity, lower yields, byproduct formation, higher capital and operation cost, corrosion problem etc. In order to make the process more economical and eco-friendly, attention needs to be given to eliminate above drawbacks.

OBJECTS OF THE INVENTION

The man object of the present invention is therefore to provide a novel process for preparation or cumene using catalytic membrane reactor that would eliminate some of the drawbacks as described above.

It is another object of the invention to provide a cumene preparation process wherein the use of excess reactant, benzene recycle/recovery cost and dilution effect are reduced.

It is another object of the invention to provide a cumene preparation process wherein operation costs are reduced, rendering the process more economical.

It is another objects of the invention to provide an eco-friendly process for the preparation of cumene.

SUMMARY OF THE INVENTION

The aims of the process of the invention of using a catalytic membrane reactor for cumene synthesis are:
i. Continuous removal of products formed which would shift the reaction equilibrium in the forward direction (Le Chatelier's principle).

ii. To decrease the feed ratio of the reactants being used. This avoids excess use of reactant, minimizes the dilution effect and reduces the benzene recycle/recovery cost.

iii. To decrease the amount of catalyst being used. Reduction in catalyst quantity would minimize reactor volume, catalyst cost and reduce operating cost against catalyst activation/regeneration utility like air, hydrogen nitrogen heat requirement etc.

iv. Elimination of byproducts (DIPB isomers, toluene $C_8$, $C_{10}$ and $C_{11}$ aromatics, n-propyl benzene, high boiling fractions). This eliminates catalyst deactivation and use of additional equipment for separation and transalkylation reaction.

v. To have product separation in the reactor itself, thereby reducing separation costs.

Accordingly, the present invention provides a process for preparation of cumene using catalytic membrane reactor, which comprises reacting isopropyl alcohol with benzene in a molar ratio of benzene to isopropyl alcohol in the range of 1:1–8:1, in catalytic membrane reactor provided with a polymeric membrane, at a temperature in the range of 190–400° C., a liquid hour space velocity (LHSV) in the range of 1 to 6 $h^{-1}$ and at a pressure of 1 to 10 bar, and separating the cumene obtained thereby.

In one embodiment of the invention, the reaction of the isopropyl alcohol with benzene is carried out in the presence of a carrier gas.

In another embodiment of the invention, the catalytic membrane is embedded with a zeolite catalyst.

In another embodiment of the invention, the catalytic membrane reactor is provided with an inert packing material.

In another embodiment of the invention, the membrane reactor comprises a vertical or horizontal flat sheet reactor or a concentric radial reactor.

In another embodiment of the invention, the reactor comprises a vertical or a horizontal flat sheet reactor provided with a polymeric membrane at a downstream side.

In another embodiment of the invention, the walls of the concentric radial type reactor is coated with a polymeric membrane.

In another embodiment of the invention, the benzene isopropanol ratio is in the range of 2:1 to 5:1, preferably in the range of 3:1 to 4:1.

In another embodiment of the invention, the reaction temperature is in the range of 200 to 240° C.

In another embodiment of the invention, the liquid hourly space velocity is in the range of 2–4 $h^{-1}$.

In another embodiment of the invention, the pressure is in the range of 1 to 4 bar.

In another embodiment of the invention, the zeolite catalyst has a Si/Al ratio of 50 to 250 preferably in the range of 100 to 250.

In another embodiment of the invention, the zeolite catalyst is selected from the group consisting of zeolite β, zeolite X and zeolite Y, preferably with a surface area of in the range of 200 to 350 $m^2/g$, preferably in the range of 250 to 300 $m^2/g$.

In another embodiment of the invention, the polymer membrane is made of polymeric material selected from the group consisting of polyimide, polyetherimide, polybenzimidazole, polyphenyl quinoxaline, polyoxazole, polyethersulfone, polyphenyleneoxide, polyetherketone, polyetheretherketone, silicone rubber containing substituent and additives, polymers obtained from olefinic monomers, copolymers and oligomers of any of the above.

In another embodiment of the invention, the inert packing material is selected from the group consisting of porcelain bead, ceramic bead, structural packing, saddle packing and inert material balls.

In another embodiment of the invention, the carrier gas is selected from the group consisting of argon, nitrogen, hydrogen and helium.

In another embodiment of the invention, the polymer membrane with or without impregnation of zeolite catalyst is obtained by preparing a solution of the polymer or oligomer or monomer in a solvent selected from the group consisting of N,N-dimethyl formamide, N,N-dimethyl acetamide, N-methylpyrrolidine, tetrachloroethane, tetrahydrofuran, chloroform, dichloromethane, toluene, hexane or any mixture thereof, filtering the solution through a sintered funnel and then pouring the filtered solution onto a flat bottomed glass surface and allowing the solvent to evaporate at ambient or elevated temperature under a controller atmosphere.

In another embodiment of the invention, additives selected from the group consisting of ammonium peroxodisulfate, 2,2'-azoisobutyronitrile (AIBN), hydrogen peroxide and benzoyl peroxide are added as desired during the membrane formation process.

In another embodiment of the invention, the walls of the radial reactor are coated with a solution of polymer/oligomer/monomer and then solvent is allowed to evaporate at definite temperature and controller atmosphere.

In another embodiment of the invention, the zeolite catalyst is embedded in the polymer membrane by adding the, zeolite in nanoparticle form to the solution of polymer or oligomer or monomers by stirring for 1 to 8 hours In another embodiment of the invention, the polymer membrane in flat sheet form with or without zeolite catalyst impregnation, is prepared by a process selected from the group consisting of compression molding, solution casting, surface coating and spinning.

In another embodiment of the invention, the polymer membrane is prepared at a temperature in the range of ambient to 200° C., preferably in the range of ambient to 150° C.

In another embodiment of the invention, the thickness of the membrane prepared is in the range of from 1–300 micron, preferably in the range of from 50–100 micron.

BRIEF DESCRIPTION OF THE ACCOMPANYING DRAWINGS

DETAILED DESCRIPTION OF THE INVENTION

Figure 1:
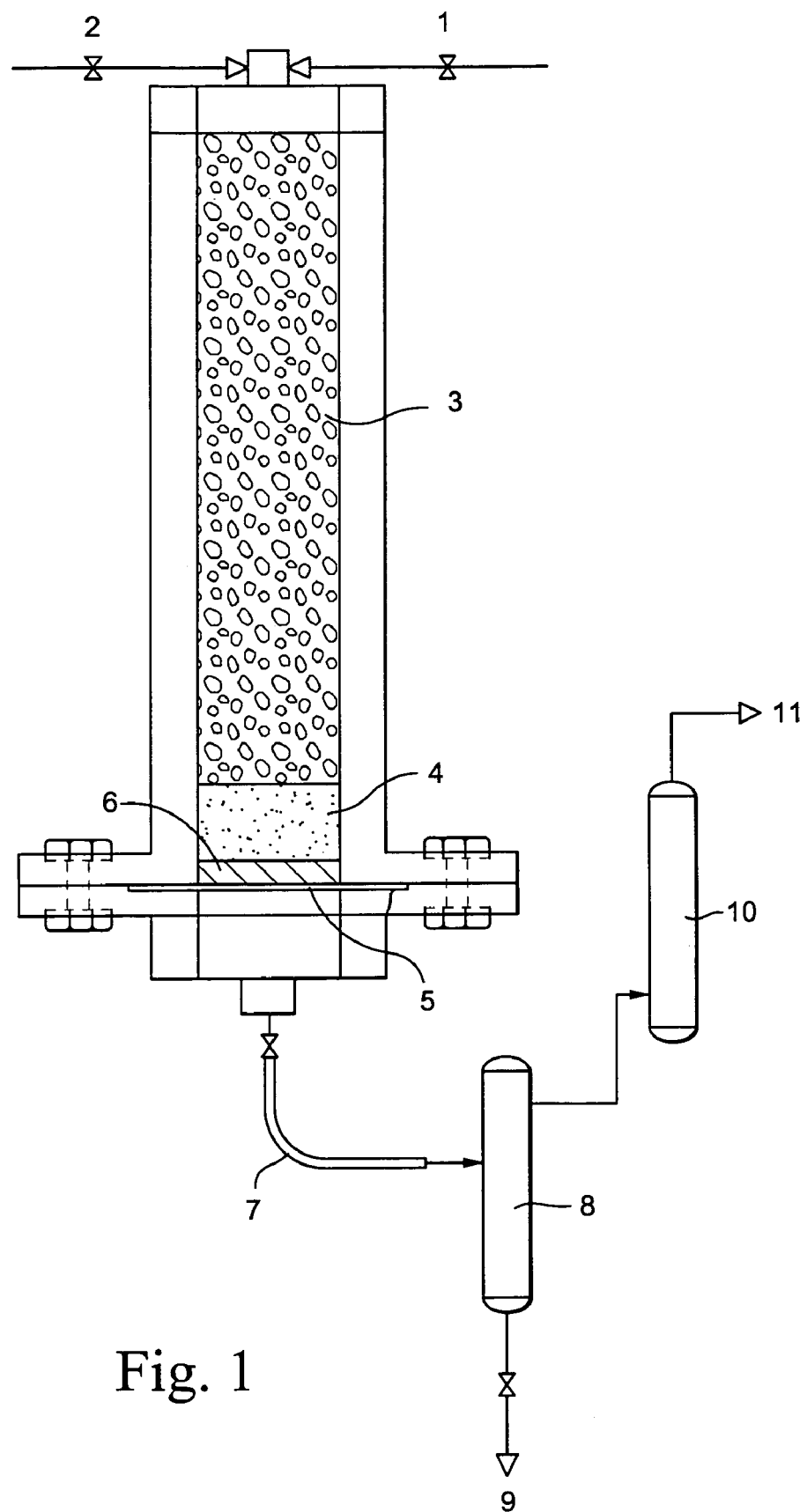
FIG. 1 is a schematic representation of a vertical flat sheet reactor used in the invention.

The present invention provides an improved process for preparation of cumene using catalytic membrane reactor, which comprises reacting isopropyl alcohol with benzene in a molar ratio of benzene to isopropyl alcohol in the range of 1:1–8:1, optionally in present of a carrier gas, in catalytic membrane reactor having polymeric membrane with or without a zeolite catalyst at a temperature in the range of 190–400° C. at a liquid hour space velocity (LHSV) in the range of 1 to 6 $h^{-1}$ and at a pressure of 1 to 10 bar optionally in presence of an inert packing material and withdrawing the products to obtain desired cumene.

The catalytic membrane reactor is vertical horizontal or concentric radial. In an another embodiment the membrane is situated at the downstream side of the vertical or horizontal flat sheet reactor whereas the walls of the concentric radial type reactor is coated with the membrane. The benzene isopropanol ratio is preferably in the range of 2:1 to 5:1 more preferably 3:1 to 4:1.

The reaction temperature used is preferably in the range of 200 to 240° C., the liquid hourly space velocity is preferably in the range of 2–4 $h^{-1}$, and the pressure used is preferably in the range of 1 to 4 bar.

The zeolite catalyst has Si/Al ratio of 50 to 250, preferably 100 to 250 exemplified by zeolite β, zeolite-X, zeolite-Y and similar zeolites. The surface area of the zeolite catalyst is preferably in the range of 200 to 350 $m^2/g$, preferably 250 to 300 $m^2/g$.

The membrane used is made of polymeric material selected from the group consisting of polyimide, polyetherimide, polybenzimidazole, polyphenyl quinoxaline, polyoxazole, polyethersulfone, polyphenyleneoxide, polyetherketone, polyetheretherketone, silicone rubber containing various substituent group and additives polymers obtained from olefinic monomers, and copolymers or oligomers of above said polymers. The membrane is impregnated with the zeolite catalyst by any conventional method. The optional inert packing material is selected from the group consisting of porcelain beads, ceramic beads, structural packing, saddle packing and inert material balls. The carrier gas is selected from the group consisting of argon, nitrogen, hydrogen and helium.

The polymer membrane (with or without impregnation of zeolite catalyst) is obtained by preparing a solution of the polymer or oligomer or monomer in a solvent selected from the group consisting of N,N-dimethyl formamide, N,N-dimethyl acetamide, N-methyl pyrrolidine, tetrachloroethane, tetrahydrofuran, chloroform, dichloromethane, toluene, hexane or any mixture thereof, filtering the solution through a sintered funnel and then pouring the filtered solution onto a flat bottomed glass surface and allowing the solvent to evaporate at ambient or elevated temperature under a controller atmosphere. Additives such as ammonium peroxodisulfate, 2,2'-azoisobutyronitrile (AIBN), hydrogen peroxide, benzoyl peroxide, and the like may be added as desired during the membrane formation process. After solvent removal, the membranes are mounted at the downstream side of the reactor. Alternatively, the solution of polymer or oligomer or monomer prepared above is coated on the porous surface of the radial reactor and then the solvent is allowed to evaporate at definite temperature and controller atmosphere.

Optionally, the zeolite catalyst is embedded in the membrane by adding the zeolite in nanoparticle form to the solution of polymer or oligomer or monomers by stirring for 1 to 8 hours. The zeolite may be added at the beginning, or after some time such that some of the monomers/oligomers have already reacted to a certain extent. In the case of obtaining flat sheet membrane for mounting at the downstream side of the reactor, the solvent is allowed to evaporate completely at a fixed temperature and under controlled atmosphere. In case of membrane formation, the wails of radial reactor, the solution of zeolite and polymer/oligomer/monomers is applied to the walls of the reactor and then the solvent evaporated completely at a fixed temperature and controlled atmosphere so that the membrane is formed at the walls of the radial reactor.

In another feature of the invention, the membrane in flat sheet form with or without catalyst impregnation, is prepared by compression molding, solution casting, surface coating, spinning or by any process that can yield a defect free membrane. The membranes are prepared at temperatures of from ambient to 200° C., preferably from ambient to 150° C. Thickness of the membrane prepared is from 1–300 micron, preferably 50–100 micron.

Figure 2:
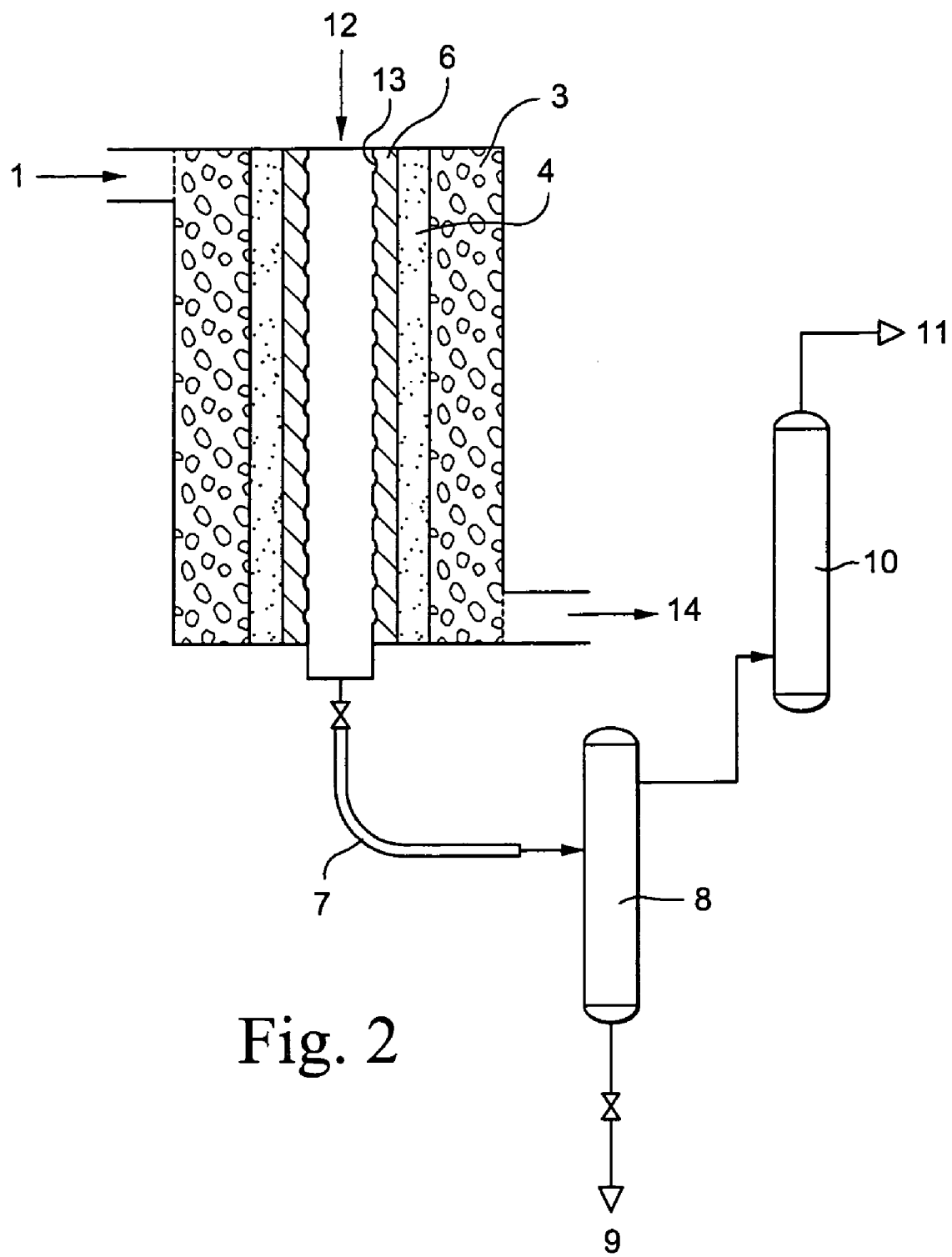
FIG. 2 is a schematic representation of a concentric radial reactor used in the invention.

The reaction of the present invention is carried out in a vertical reactor (shown in FIG. 1) or radial type reactor (shown in FIG. 2) wherein the various components are:

| | |
|---|---|
| 1: | feed stream |
| 2: | inert gas inlet |
| 3: | inert packing material |
| 4: | catalyst bed |
| 5: | perforated sheet |
| 6: | membrane |
| 7: | condenser |
| 8: | first stage separator |
| 9: | product stream |
| 10: | second stage separator |
| 11: | vent |
| 12: | sweep gas (optional) |
| 13: | porous tube |
| 14: | reject effluent. |

The process of the present invention is described below by the following illustrative which should not be considered to limit the scope of the present invention in any manner.

EXAMPLE 1

8% solution of polyphenylene oxide (PPO) is prepared in toluene by dissolving the polymer with stirring at ambient conditions for 8 hours, filtering through sintered funnel, degassing and then poured onto a flat bottomed glass surface and then kept under humidity and temperature controlled atmosphere for initial evaporation of solvent. This resulted in a membrane with a thickness of 150 microns. In order to ensure complete removal of solvent, the membrane was dried in vacuum over for 24 hours and then used for mounting at downstream side of the catalytic membrane reactor.

EXAMPLE 2

4% solution of silicon rubber (SR) was prepared by dissolving in chloroform with stirring for 4 hrs. Benzoyl peroxide (3% by wt. of SR) was added to this solution. Stirring was continued for half an hour, followed by filtering and pouring of filtered solution on a flat glass surface for solvent evaporation under controlled temperature and humidity. After complete evaporation of the solvent, the dried film was kept in a muffle furnace at 120° C. for 3 hours. After this treatment a clean transparent film was obtained. The film was again given an oven treatment at about 40° C. for half an hour. Thickness of membranes obtained was around 60 μm. The membrane was mounted at the downstream end of the catalytic membrane reactor.

EXAMPLE 3

2% solution of silicon rubber (SR) was prepared by dissolving in toluene with stirring for 4 hrs. Benzoyl peroxide (3% by wt. of SR) was added to this solution. Stirring was continued for an hour followed by filtering and pouring of solution on a flat glass surface for solvent evaporation under controlled temperature and humidity. After complete evaporation of the solvent, the dried film was kept in a muffle furnace at 120° C. for 3 hours. After this treatment, a clean transparent film was obtained. The film was again given an oven treatment at about 40° C. for half an hour. Thickness of membranes obtained was around 130 μm. This membrane was use for mounting at the downstream of the catalytic membrane reactor.

EXAMPLE 4

A 3% solution of polyetherimide (PEI) was prepared by dissolving it in 80:20 mixture of N,N-dimethyl formamide and N-methylpyrrolidone with stirring for 10 hours at 60° C. and ambient pressure and dry atmosphere. Resulting solution was then filtered through sintered funnel, degassed and poured onto flat glass surface for solvent evaporation at 80° C. under controlled humidity. After complete evaporation of solvent, dried film was kept in a vacuum oven at 120° C. for 5 days. Average thickness of the membranes obtained was 100 μm. This membrane was used for mounting at the downstream of the catalytic membrane reactor.

EXAMPLE 5

A 3% solution of polybenzimidazole was prepared by dissolving it in a mixture of N,N-dimethyl acetamide and N-methyl pyrrolidone with stirring for 10 hours at ambient conditions. Resulting solution was then filtered through sintered funnel, degassed and then poured onto flat glass surface for solvent evaporation at 120° C. After complete evaporation of the solvent, the dried film was kept in the vacuum oven at 120° C. for 5 days. The average thickness of the membranes thus obtained was 170 μm. This membrane was used for mounting at the downstream of the catalytic membrane reactor.

EXAMPLE 6

The benzene isopropylation reaction was carried out in a catalytic membrane reactor, with reactants (Betzene:IPA) mole ratio of 3:1, space velocity of 2.4 h$^{-1}$, reaction temperature of 210° C. and a catalyst volume of 2.2 cc per 100 cc of reactor volume. The similar IPA conversion i.e. 99.53% was observed with CMR as compared to conventional zeolite based fixed bed reactor process. The selectivity towards cumene was observed to be 100% with CMR, as against 91.9% with the conventional process. The total selectivity (cumene+DIPB) was observed to be 100% with CMR, as against conventional process. The reactants (IPA: benzene) mole ratio used was 2.16 times lower than the conventional process. Catalyst volume/reactor volume ratio used was half i.e. 0.5 times lower as compared to conventional process. The results are presented in Table 1.

TABLE 1

Comparative Results on CMR with Conventional Reactor

| Parameter | Conventional reactor | Vertical CMR as in Example No. 6 | Vertical CMR as in Example No. 7 | Vertical CMR as in Example No. 8 |
|---|---|---|---|---|
| Mole Ratio (IPA Benzene) | 1:6.5 | 1:3 | 1:3 | 1:2 |
| Catalyst volume (cc) 100 cc Reactor | 4.4 | 2.2 | 2.6 | 3.0 |

TABLE 1-continued

Comparative Results on CMR with Conventional Reactor

| | Conventional reactor | Vertical CMR as in Example No. 6 | Vertical CMR as in Example No. 7 | Vertical CMR as in Example No. 8 |
|---|---|---|---|---|
| Volume LHSV (h$^{-1}$) | 2.5 | 2.4 | 3.6 | 3.6 |
| Reaction Temperature (° C.) | 210 | 210 | 210 | 220 |
| GC Product Distribution: | | | | |
| Aliphatics | 0.17 | 0.007 | 0.17 | 0.16 |
| Benzene | 78.40 | 80.2 | 70.99 | 72.57 |
| Cumene | 19.86 | 18.81 | 17.87 | 20.07 |
| Toluene C$_8$ Aromatics | 0.30 | 0 | 0 | 0 |
| n-Propylbenzene | 0.07 | 0 | 0 | 0 |
| C$_{10}$ C$_{11}$ Aromatics | 0.09 | 0 | 0 | 0 |
| DIPB | 1.01 | 0 | 0 | 0 |
| High boiling fractions | 0.11 | 0 | 0 | 0 |
| IPA Conversion (wt %) | 99.8 | 99.53 | 99.66 | 96.83 |
| Cumene Selectivity (%) | 91.9 | 100 | 100 | 100 |

EXAMPLE 7

In an another example, the reaction was carried out in the catalytic membrane reactor at a space velocity of 3.6 h$^{-1}$. The mole ratio (benzene:IPA) was 3:1, with a reaction temperature of 210° C. and the catalyst volume of 2.6 cc per 100 cc of reactor volume. The same conversion i.e. 99.6% was observed with CMR as compared to conventional process. The cumene selectivity was observed to be 100% as against 91.9% with conventional process. The total (cumene+DIPB) selectivity was observed to be 100% as compared to 96.9% with conventional process. The reaction used almost half ratio of the catalyst volume/reactor volume ie. 2.6 as against 4.4 with conventional process, which helps to minimize byproduct formations, prolong the catalyst life and reduce reactant feed requirement. The results are tabulated in Table 1.

EXAMPLE 8

The reaction was carried out at a mole ratio (benzene:IPA) of 2:1, using catalytic membrane reactor. The reaction temperature used at 220° C., with a space velocity of 3.6 h$^{-1}$. The catalyst volume used is 3 cc per 100 cc of reactor volume. The comparable IPA conversion i.e. 98.83% was observed as against 99.8% with conventional process. The cumene and total (cumene+DIPB) selectivity was observed to be 100% as against 91.9% and 96.9% respectively, with the conventional process. The reaction used 3.25 times lower reactant feed ratio as compared to conventional process. The catalyst/reactor volume ratio used was 1.46 times lower than the conventional process. The LHSV used was 1.44 times lower as against conventional process. The results are presented in Table 1.

From Table 1, Following Inferences are Drawn:

1. It is evident from examples 6 to 8 that cumene selectivity observed to be 100% by using CMR as against 91.6% with conventional reactor.
2. In CMR, reaction proceeds in forward direction (Le Chatelier's Pinciple), thereby avoiding the formation of DIPB, giving selectivity for the desired product i.e. cumene. This avoids the step of transalkylation of DIPB to cumene, ultimately resulting in reduction in capital investment, operating cost, plant space and process complexities.

3. Byproduct formation like toluene+$C_8$ Aromatics, n-propylbenzene. $C_{10}C_{11}$ Aromatics, high boiling fractions is completely eliminated with CMR, while the same are significant with conventional reactor.
4. The catalyst mass required for CMR is half that that for conventional reactor. Thus by using CMR the size of the reactor can be reduced.
5. The feed dilution is minimized by using CMR, which is evident by the mole ratio (IPA:Benzene) required as just 1.2–3 as against minimum 1:6.5 with conventional reactor. This less dilution also has a great impact on cost reduction of quantity of benzene required, recycle equipment operational cost, etc.
6. In CMR, space velocity found to be 3.6 $h^{-1}$ as against 2.5 $h^{-1}$ with conventional reactor. This increase in space velocity helps minimizing byproduct formation and also improves catalyst and membrane efficiency.
7. In CMR, the reaction and separation can be achieved in one column, thereby reducing the capital investment cost.
8. In all the cases, cumene+DIPB selectivity observed to be 100% for CMR, as against 6.9% for conventional reactor.
9. By using CMR, the % conversion is similar (~99.8%) as in case of conventional reactor. However, CMR offers excellent features as discussed above which ultimately has a great impact on the process economics.
10. By using CMR, isopropylation of benzene to cumene becomes a clean and eco-friendly process, as byproducts formation is completely avoided.

Advantages:

The process for preparation of cumene using catalytic membrane reactor has the following advantages:

ii. Using membrane reactor as postulated herein, product formed is removed continuously. This continuous removal shifts the reaction equilibrium in the forward direction (Le Chatelier's principle). This also makes the product (cumene) unavailable for the farther reactions which lead to byproduct formation.

iii. Mole ratio of the feed components is reduced to half in comparison to a zeolite based process. Thus dilution effect is minimized, reducing the benzene recycle/recovery cost.

iv. The space velocity using the membrane reactor is increased by 1.5 times in comparison with the conventional reactor that uses zeolite. This increases reaction rate, prolongs life of the catalyst and reduces the reactant quantity per unit volume of the catalyst.

v. An amount of catalyst required in the membrane reactor is reduced to half than the same required in the conventional reactor. This ultimately leads to the reduction in reactor volume, amount of catalyst and operating cost.

vi. Formation of byproduct (DIPB isomers, toluene, $C_8$, $C_{10}$ and $C_{11}$ aromatics, n-propyl benzene, high boiling fractions) is completely eliminated. Absence of byproducts reduces possibility of catalyst deactivation. Also additional steps for separation and transalkylation reaction are eliminated or minimized.

We claim:

1. A process for preparation of cumene using a catalytic membrane reactor, which comprises reacting isopropyl alcohol with benzene in a molar ratio of benzene to isopropyl alcohol in the range of 1:1–8:1, in the catalytic membrane reactor provided with a polymeric membrane, at a temperature in the range of 190–400° C., a liquid hour space velocity (LHSV) in the range of 1 to 6 $h^{-1}$ and at a pressure of 1 to 10 bar, and separating the cumene obtained thereby with the polymeric membrane.

2. A process as claimed in claim 1 wherein the reaction of the isopropyl alcohol with benzene is carried out in the presence of a carrier gas.

3. A process as claimed in claim 1 wherein the polymeric membrane is embedded with a zeolite catalyst.

4. A process as claimed in claim 1 wherein the catalytic membrane reactor is provided with an inert packing material.

5. A process as claimed in claim 1 wherein the membrane reactor comprises a vertical or horizontal flat sheet reactor or a concentric radial reactor.

6. A process as claimed in claim 5 wherein the reactor comprises a vertical or a horizontal flat sheet reactor provided with the polymeric membrane at a downstream side thereof.

7. A process as claimed in claim 5 wherein the walls of the concentric radial type reactor are coated inside the reactor with the polymeric membrane.

8. A process as claimed in claim 1 wherein the benzene: isopropanol ratio is in the range of 2:1 to 5:1.

9. A process as claimed in claim 1 wherein the benzene: isopropanol ratio is in the range of 3:1 to 4:1.

10. A process as claimed in claim 1 wherein the reaction temperature is in the range of 200 to 240° C.

11. A process as claimed in claim 1 wherein the liquid hourly space velocity is in the range of 2–4 $h^{-1}$.

12. A process as claimed in claim 1 wherein the pressure is in the range of 1 to 4 bar.

13. A process as claimed in claim 3 wherein the zeolite catalyst has a Si/Al ratio of 50 to 250.

14. A process as claimed in claim 13 wherein the zeolite catalyst has a Si/Al ratio in the range of 100 to 250.

15. A process as claimed in claim 3 wherein the zeolite catalyst is selected from the group consisting of zeolite β, zeolite X and zeolite Y.

16. A process as claimed in claim 13 wherein the surface area of the zeolite catalyst is in the range of 200 to 350 $m^2/g$.

17. A process as claimed in claim 13 wherein the surface area of the zeolite catalyst is in the range of 250 to 300 $m^2/g$.

18. A process as claimed in claim 1 wherein the polymer membrane is made of polymeric material selected from the group consisting of polyimide, polyetherimide polybenzimidazole, polyphenyl quinoxaline, polyoxazole, polyethersulfone, polyphenyleneoxide, polyetherketone, polyetheretherketone, silicone rubber containing substituent and additives, polymers obtained from olefinic monomers, copolymers and oligomers of any of the above polymers.

19. A process as claimed in claim 4 wherein the inert packing material is selected from the group consisting of porcelain bead, ceramic bead, structural packing, saddle packing and inert material balls.

20. A process as claimed in claim 2 wherein the carrier gas is selected from the group consisting of argon, nitrogen, hydrogen and helium.

21. A process as claimed in claim 18 wherein the polymer membrane with or without impregnation of zeolite catalyst is obtained by preparing a solution of the polymer or oligomer or monomer in a solvent selected from the group consisting of N,N-dimethyl formamide, N,N-dimethyl acetamide, N-methyl pyrrolidine, tetrachloroethane, tetrahydrofuran, chloroform, dichloromethane, toluene, hexane or any mixture thereof, filtering the solution through a sintered funnel and then pouring the filtered solution onto a flat bottomed glass surface and allowing the solvent to evaporate at ambient or elevated temperature under a controlled atmosphere.

22. A process as claimed in claim 21 wherein additives selected from the group consisting of ammonium peroxodisulfate, 2,2'-azoisobutyronitrile (AIBN), hydrogen peroxide and benzoyl peroxide are added as desired during the membrane formation process.

23. A process as claimed in claim 7 wherein the walls of the concentric radial reactor are coated inside the reactor with a solution of polymer/oligomer/monomer and then solvent is allowed to evaporate at definite temperature and controlled atmosphere.

24. A process as claimed in claim 3 wherein the zeolite catalyst is embedded in the polymer membrane by adding the zeolite in nanoparticle form to the solution of polymer or oligomer or monomers by stirring for 1 to 8 hours.

25. A process as claimed in claim 1 wherein the polymer membrane in flat sheet form with or without zeolite catalyst impregnation, is prepared by a process selected from the group consisting of compression molding, solution casting, surface coating and spinning.

26. A process as claimed in claim 25 wherein the polymer membrane is prepared at a temperature in the range of ambient to 200° C.

27. A process as claimed in claim 25 wherein the polymer membrane is prepared at a temperature in the range of ambient to 150° C.

28. A process as claimed in claim 25 wherein the thickness of the membrane prepared is in the range of from 1–300 micron.

29. A process as claimed in claim 25 wherein the thickness of the membrane prepared is in the range of from 50–100 micron.

* * * * *